(12) United States Patent
Haddad

(10) Patent No.: US 7,109,035 B2
(45) Date of Patent: Sep. 19, 2006

(54) SYNTHETIC URINE AND METHOD OF MAKING SAME

(76) Inventor: Laith Haddad, 230 Bunker CT, Alpharetta, GA (US) 30004

( * ) Notice: Subject to any disclaimer, the term of this patent is extended or adjusted under 35 U.S.C. 154(b) by 471 days.

(21) Appl. No.: 10/608,992

(22) Filed: Jun. 27, 2003

(65) Prior Publication Data

US 2004/0077106 A1    Apr. 22, 2004

Related U.S. Application Data

(60) Provisional application No. 60/393,574, filed on Jul. 2, 2002.

(51) Int. Cl.
 *G01N 33/48* (2006.01)
 *G01N 33/493* (2006.01)
 *G01N 33/50* (2006.01)
(52) U.S. Cl. .............. 436/8; 436/19; 436/159
(58) Field of Classification Search .......... 436/8, 436/19, 159
 See application file for complete search history.

(56) References Cited

U.S. PATENT DOCUMENTS

| 4,024,256 | A | * | 5/1977  | Griffith et al. ......... 514/244 |
| 4,590,800 | A | * | 5/1986  | Shimoda ................. 73/449 |
| 4,714,564 | A | * | 12/1987 | Lynch et al. ............ 510/402 |
| 4,825,851 | A | * | 5/1989  | Cocks et al. ............ 601/4 |
| 5,100,807 | A | * | 3/1992  | Adamczyk et al. ...... 436/543 |

* cited by examiner

*Primary Examiner*—Jean C. Witz
(74) *Attorney, Agent, or Firm*—Womble Carlyle Sandridge & Rice, PLLC

(57) ABSTRACT

A synthetic urine formulation, a kit including the synthetic urine formulation and a method of preparing synthetic urine are described. The urine formulation includes urine components in dried form, concentrated form or normal concentration and a compound that, when added to water, increases the temperature of the water (a "heat activator"). When the urine components are present in dried form, the synthetic urine can be provided in one or two parts. When present in concentrated form or in normal concentration, the heat activator must be provided separately. Lithium chloride is a preferred heat activator. The components can be provided in kit form, including a measuring cup with a fill line, the powdered, concentrated or normal concentration synthetic urine components, and the heat activator. Optionally, but preferably, the kit also includes a temperature measuring device to ensure that the appropriate temperature is reached. The synthetic urine formulation includes an appropriate amount of individual components of human urine such that the sample can appear to be a genuine human urine sample, with components testing within normal limits.

17 Claims, No Drawings

SYNTHETIC URINE AND METHOD OF MAKING SAME

The application claims priority to U.S. Ser. No. 60/393,574, filed on Jul. 2, 2002, entitled "Synthetic Urine and Method of Making Same," the contents of which are hereby incorporated by reference in their entirety.

FIELD OF THE INVENTION

The invention is directed to a composition of synthetic urine, a kit comprising synthetic urine and a method of using the same, wherein the synthetic urine composition has characteristics of human urine.

BACKGROUND

Urine samples are routinely tested for medical identification of illness or drug abuse. Manufacturers of urine assay kits typically ask their employees to donate urine samples, then pool and treat the samples to manufacture appropriate controls. It is difficult to obtain a large pool of consistent quality, in part because the employees drink varying amounts of coffee, take varying amounts of prescription and over-the-counter medication, and/or take vitamins. Urine also has an odor that makes it disagreeable for most chemists to work with.

Synthetic urine samples have been developed to assure that the instrumentation used to test urine samples is working properly. However, urine tests also routinely require that the urine samples are at a specified range of temperatures, at or near body temperature, at the time of collection, and the synthetic urine samples are stored at room temperature.

Synthetic urine samples have also been developed for defeating drug tests as well as protecting people from genetic profiling without their consent. These urine samples are also typically stored at room temperature by individuals seeking to pass a drug test, and therefore will not be accepted for testing by laboratories that test the temperature of the urine samples. Some individuals who might test positive for the presence of drugs or be subjected to undesired genetic screening if they were to provide their own urine spend all day, every day, walking around with a sample of synthetic urine stored under their armpit or between their thighs so that it is always at body temperature. This is an inconvenient means for providing urine samples at the appropriate temperature, and is not suitable for laboratory use.

It would be advantageous to provide a synthetic urine that can be stored at room temperature in dried or concentrated form and mixed with water to provide a synthetic urine sample that is within an acceptable temperature range for use in drug screening tests. The present invention provides such a synthetic urine.

SUMMARY OF THE INVENTION

A synthetic urine formulation, a kit including the synthetic urine formulation and a method of preparing synthetic urine are described. The urine formulation includes urine components in dried form, concentrated form or normal concentration and a compound that, when added to water, increases the temperature of the water (a "heat activator"). When the urine components are present in dried form, the synthetic urine can be provided in one or two parts, wherein one part includes the synthetic urine components and the other part includes the heat activator. When the urine components present in concentrated form or in normal concentration, the heat activator must be provided separately.

In use, a pre-measured amount of synthetic urine components and heat activator are added to a pre-determined amount of room temperature water, and the heat activator heats the resulting synthetic urine to a temperature approximating body temperature. The heat activator can be added before, with or after the synthetic urine components are added to the water. Alternatively, the synthetic urine components can be stored in an appropriate amount of water, and the heat activator added to bring the synthetic urine to a temperature approximating body temperature.

The components can be provided in kit form, including a measuring cup with a fill line, the powdered or concentrated synthetic urine components, and the heat activator. Optionally, but preferably, the kit also includes a temperature measuring device to ensure that the appropriate temperature is reached. Examples of temperature measuring devices include temperature sensitive labels and disposable plastic strips that turns different colors at different temperatures. The kit can also include a mixing container.

The synthetic urine formulation includes an appropriate amount of individual components of human urine such that the sample can appear to be a genuine human urine sample, with components testing within normal limits. Colorants can be added, as appropriate, to ensure that the urine color is in the correct range. In one embodiment, the synthetic urine is or includes dried or concentrated human urine.

The invention will now be described in detail with regard to specific embodiments.

DETAILED DESCRIPTION OF SPECIFIC EMBODIMENTS

Synthetic urine formulations are useful for calibration of diagnostic equipment. A synthetic urine formulation has advantages of known characteristics of pH, specific gravity, creatine level and the like, for testing of diagnostic equipment. Further, a synthetic urine formulation of laboratory grade chemicals is safe for handling because there is no risk of disease. For maximum usefulness, it is desirable to have a synthetic urine formulation which can be stored indefinitely before use and be prepared quickly when needed. Further, it is desirable that the synthetic urine formulation be easily prepared without the need for exotic chemicals, solvents or complicated procedures.

Synthetic Urine Composition

Normal urine is a highly complex aqueous solution of organic and inorganic substances. The majority of the constituents are either waste products of cellular metabolism or products derived directly from certain foods that are eaten. The typical ratio of organic to inorganic products is about 3.5/2.5, although these ranges typically vary from subject to subject.

The most important organic substances are urea, uric acid and creatinine. Urea constitutes about ninety-five percent of the nitrogen content of urine, so it is not typically necessary to include uric acid. Creatinine is a hydrated form of creatine. There may be twice as much creatinine as uric acid in the urine. In some embodiments, it is preferable to include creatinine in approximately normal levels in the synthetic urine sample.

The principle inorganic constituents of urine are chlorides, phosphates, sulfates and ammonia. Sodium chloride is the predominant chloride and makes up about half of the inorganic substances. Since ammonia is toxic to the body and lacking in plasma, there is very little of it normally present in fresh urine. Accordingly, the synthetic urine sample need not, but may, include a small amount of ammonia to simulate the ammonia present in normal urine that is allowed to stand at room temperature for 24 hours or longer that is formed by the breakdown of urea by bacterial action.

In use, the synthetic urine ideally has a temperature in the range of 90 to 100° F. so that it can pass as an acceptable urine specimen. The synthetic urine formulation, when diluted with an appropriate amount of water, has a specific gravity between about 1.00 and 1.035 and a pH between about 4 and 9, preferably between about 5 and 10. Preferably, the total solids content is between about 1.5 and 6% by weight. When diluted, the synthetic urine includes at least urea and water, and optionally includes a buffer, such as a phosphate buffer, uric acid, creatine or creatinine, and a source of sodium, potassium, phosphorus and/or calcium ions in ranges typical of a human urine sample.

In one embodiment, the synthetic urine includes between 1 and 3, preferably about 2 grams/liter of potassium chloride, between 1 and 3, preferably about 2 grams/liter of sodium sulfate, between 0.5 and 1.5, preferably about 0.85 grams/liter of ammonium phosphate, preferably about 0.85 grams/liter of ammonium diphosphate, preferably about 0.15 and 0.5, preferably about 0.25 grams/liter of calcium chloride, and between about 0.25 and 1, preferably about 0.5 grams/liter of magnesium chloride.

In one embodiment, the synthetic urine includes between about 60–90 mg/dl of urea, which is the normal range of urea in urine. The concentration of creatinine, when present, is preferably above about 5 mg/dl, and more preferably, between about 37 and 300 mg/dl.

Those of skill in the art can readily determine the appropriate ranges of these components in a typical urine sample. Indeed, the sample can even be a freeze-dried human urine sample.

At least urea and creatinine are preferably present, ideally in a suitable range for a human urine sample. Optional components include a suitable preservative, and testosterone or estrogen, in appropriate amounts such that the urine sample passes for a human urine sample. Also, a suitable coloring agent, such as beta carotene, yellow dyes, vitamin B12, and the like, can be added.

If desired, the synthetic urine specimen can be doped with an appropriate amount of a substance tested for in urinalyses, to confirm that the testing equipment is functioning properly. Such substances include, without limitation, THC or its major metabolite THCA, deuterated THCA, opiates such as heroin and morphine, PCP, amphetamine, cocaine or its major metabolite benzoyl ecgonine, ethanol, acetaldehyde and the like. To the extent that it is possible that other substances could be mistaken for these substances, such as acetominophen or acetyl salicylic acid, these substances can be added and the "doped" synthetic urine used as a negative control in urinalyses.

The synthetic urine can be stored in powdered form, concentrated form, or at normal concentration. When stored in powdered form, the synthetic urine can be mixed with the heat activator, or provided separately. When stored in concentrated form or at normal concentration, the heat activator must be stored separately so that it can be mixed with the synthetic urine components and heat the components to the desired temperature. For maximum length of storage and efficient storage space, a dried urine composition is desirably used, and added to water to form a urine solution when needed.

When concentrated, the composition can be in the form of a liquid, gel or paste. The concentrated urine composition can include a carrier, such as a pectin matrix, which is dissolvable in water provided the carrier will not result in abnormal urine readings when tested.

Buffer

Urine typically has a pH in the range of between 4 and 9, more typically between about 5 and 8. The human body typically buffers urine with a phosphate buffer. Accordingly, the preferred buffer is a phosphate buffer at an appropriate concentration to keep the pH of the synthetic urine in the range of between about 5 and 8. Other suitable buffers include citrate buffers, HEPES buffer, TRIS buffer, and other buffers known in the art, for example, those buffers used to keep cell culture media at appropriate pH levels.

Packaging

The urine composition is preferably packaged for storage in an airtight container. Such container can include a sealed pouch of plastic, plastic-lined foil, waxed paper or the like, or a vial or any other suitable container as known to practitioners in the art. The container is advantageously formed of materials which do not react with the components of the urine composition, for example, glass or plastic. The container can include a cap of screw-on, pressure fit, flip top, or any other known configuration so long as an airtight seal is provided. Alternately, the container can be sealed and scored so that one end can be broken to expose the contents. The concentrated urine composition can be stored for an extended period of time, i.e., about a year, without loss of normal human urine characteristics so long as oxidation is avoided or at least minimized. Thus, desirably, after packaging and before sealing, the headspace of the container is flushed with a gas that is non-reactive with the concentrated urine composition, such as carbon dioxide, nitrogen, or other gases known to practitioners in the art.

Methods of Forming and Using the Synthetic Urine Composition

To form a urine solution, the contents of a package of dried or concentrated urine composition are mixed with water, preferably with stirring, shaking or mixing. For ease of dissolution, it is desirable that the water be at least at room temperature.

The urine solution, whether provided as a solution or made fresh from a dried or concentrated urine composition mixed with the appropriate amount of water, has the following characteristics, which are characteristics of normal human urine:

pH: about 4.0–9.0, desirably about 4.5–8.0, more desirably about 5.0–7.5 creatinine within normal range, specific gravity: about 1.005–1.035, desirably about 1.010–1.020 color: pale yellow—dark yellow; desirably yellow clarity: clear, not cloudy

Heat Activator

To bring the urine solution to approximately body temperature for use, a heat activator is added. The heat activator is a chemical which reacts with water exothermically, producing heat and raising the temperature of the water. The heat activator does not react with the synthetic urine components, does not noticeable effect the urine characteristics, notably color, odor, specific gravity, pH and creatinine level, and does not produce any byproducts or residues not found in normal human urine. The heat activator is preferably non-toxic and/or safe for human handling.

The heat activator is desirably provided in a granule or powder form. Suitable heat activators include, but are not limited to, lithium chloride, silica gel, molecular sieves, acids such as sulfuric acid, hydrobromic acid, hydroiodic acid, hydrofluoric acid, hydrochloric acid, nitric acid, and the like, alkali bases such as sodium, potassium, calcium and lithium hydroxide, other lithium salts such as lithium bromide, lithium perchlorate and the like, and fluoride salts, such as lithium, cesium, rubidium, and potassium fluoride. The acids and bases can be combined in a manner in which they generate a sufficient amount of heat but the acid and base neutralize each other such that the urine pH is within normal range.

Typically, the heat activators are hygroscopic in nature, such that they have a high heat of solution. Other suitable heat activators will be apparent to practitioners in the art. Desirably, the heat activator is lithium chloride.

Water has a heat capacity of one calorie per gram degree C. Accordingly, with knowledge of the volume of the water to be added (adjusted to account for the added components), the approximate starting temperature, and the heat of solution of the heat activator, those of skill in the art can readily determine an appropriate amount of a heat activator to add to the synthetic urine components to bring the urine to a temperature in the range of about 90 to 100° F.

The heat activator is used in an amount sufficient to heat the urine solution to about body temperature, from about 90° F. to about 100° F. The amount of heat activator necessary to heat the solution to the desired level will be expected to depend on the quantity of urine solution to be heated, the starting temperature of the urine solution and the specific heat activator used. Given these factors, the amount of heat activator necessary to raise the urine solution to a desired temperature is readily determinable by practitioners in the art.

The heat activator, being hygroscopic in nature, is advantageously provided in a sealed container such as an airtight pouch or airtight vial as described above for use with the dried urine composition. Desirably, the container is flushed with a non-reactive gas as known to practitioners in the art, such as carbon dioxide or nitrogen, before sealing in order to remove any remaining atmosphere and water vapor. Flushing with carbon dioxide is preferred.

Synthetic Urine Kit

For convenience, the synthetic urine formulation and heat activator can be provided as a kit. A kit includes synthetic urine formulation in dried, concentrated or solution form, heat activator, and a container suitable for mixing the urine solution and heat activator. If dried or concentrated urine composition is used, the mixing container is also suitable for addition of an appropriate amount of water, i.e., an amount between about 2 and about 5 ounces, preferably about 3 ounces. The kit includes sufficient amounts of synthetic urine formulation and heat activator to provide a synthetic urine formulation at about body temperature.

Container

The mixing container is advantageously provided in a suitable urine sample size, for example, between about 2 ounces (60 mL) and about 5 ounces (150 ml), preferably about 3 ounces (90 mL). The mixing container can be a container capable of tight closure or an open container, in which case a means of stirring the urine solution is necessary, such as a plastic or glass stirrer. Desirably, a closable container is used, such as a sealable pouch, a sealable vial, or other container as described elsewhere herein. The container can have sealing means as known to practitioners in the art. For example, a pouch can have intermeshing ribs or a tie closure, and a vial or other container can have a stopper or fitted cap, wherein the cap is closable by interlocking threads (screw-on top), pressure fit, flip top, or any other mechanism known to practitioners in the art.

In use with a dried or concentrated urine composition, water is added to the mixing container in an appropriate amount to form a synthetic urine formulation of normal human urine characteristics. Thus, it is desirable to provide a demarcation on the container to indicate the correct fluid level so that separate measurement of the water is not necessary. In one embodiment, the line of demarcation, or fill line, is the top of a temperature measuring strip adhered to the container. The mixing container can be the container including the dried or concentrated urine composition. If the synthetic urine formulation is provided as a solution, it is desirable that the solution bottle itself be used as the mixing container.

It is further desirable to have a temperature indicator on the mixing container so that the user will know when the solution is in the desired temperature range of from about 90° F. to about 100° F. Desirably, the temperature indicator covers a temperature range of from about 80° F. to about 110° F., desirably about 90° F. to about 100° F., indicating change in temperature by change in color, movement of an indicator line, or the like as known to practitioners in the art. Alternatively, a temperature sensing probe such as but not limited to a thermometer can be used to determine the temperature of the solution.

Urine Formulation

Dried or concentrated urine composition is provided in the kit in an amount sufficient to create a synthetic urine formulation with normal human urine characteristics in the amount of the mixing container. The dried urine is provided in an amount sufficient such that, when diluted, approximates an actual urine sample. The amount concentrated urine composition needed to prepare a synthetic urine formulation will vary depending on the concentration strength, and is readily determinable by practitioners in the art.

A urine solution can be provided in a concentration and amount sufficient for the desired sample size, typically between about 2 ounces and about 5 ounces (about 60 ml to about 150 ml), preferably about 3 ounces (90 mL).

Method of Forming Synthetic Urine

The synthetic urine is formed using the ingredients described herein, namely a synthetic urine formulation and a heat activator as needed. When the synthetic urine formulation is in dried or concentrated form, water is also used. The ingredients can be supplied in the form of a kit, or separately acquired.

Using Dried Urine

Dried urine composition is mixed with an appropriate amount water to create a urine sample of the desired size with the characteristics of normal human urine. Desirably, the water and dried urine composition are poured into a container suitable for mixing. Alternately, the water can be added to the dried urine composition if the dried urine composition is provided in a container of sufficient size. Desirably, the dried urine composition is added to the water. The container is sealed and shaken gently to promote dissolution of the dried urine composition. If it is an open container, the contents are stirred with a non-reactive material. The urine solution is properly mixed when clear and without visible sediment. To aid dissolution of the dried urine composition, warm water is desirably used. Desirably, water at a temperature range of from about 70° F. to about 90° F. is used for mixing with the dried urine composition.

Using Concentrated Urine Solution

If a concentrated urine composition is used, the concentrated urine composition is diluted with an appropriate amount of water to create a urine solution of the desired size with the characteristics of normal human urine. The water and concentrated urine composition can be mixed in a separate container, or the water can be added to the container of concentrated urine composition if the concentrated urine composition is provided in a container of sufficient size. The container is sealed and shaken gently to promote dilution of the concentrated urine composition. If it is an open container, the contents are stirred with a non-reactive material. The urine solution is properly mixed when clear and without visible sediment. Desirably, the water for dilution is at a temperature range of from about 70° F. to about 90° F.

Adding Heat Activator

Once the urine solution is formed from dried or concentrated urine composition, or starting with a urine solution already having characteristics of normal human urine, a heat activator is added as needed to the urine solution to bring it within normal body temperature range. Desirably, the heat activator is added slowly with swirling, stirring or gentle shaking until the desired temperature is achieved. The heat activator is dissolved when the solution appears clear and is without sediment. A temperature probe should be used to monitor the temperature of the solution while adding the heat activator, or a temperature gauge on the container itself can be used to ensure that neither too little nor too much heat activator is added. The resultant urine solution should have a temperature in the range of from about 85° F. to about 105° F., desirably from about 90° F. to about 100° F. It is noted that if the water used to dilute the dried or concentrated urine composition is of a sufficient temperature, use of all of the heat activator is not required. In some instances, tap water can be obtained hot enough that no heat activator is necessary. Excess heat activator can be appropriately discarded.

The heat activator can be added to the dried or concentrated urine composition before mixing with water if desired. The heat activator can also be packaged with the dried urine composition if desired. However, in such cases, care should be taken to add water of about room temperature to the urine composition to avoid overheating the resultant urine solution.

If the urine solution is above the desirable temperature range after adding the heat activator, the solution can be cooled by setting on a flat surface and stirring gently, or running cold water over the outside of the container, with frequent stops to stir the solution and check the temperature. If the solution is below the desirable range, it can be warmed by holding against the body, desirably under the arms or between the thighs, or by running hot water on the outside of the container, with frequent stops to stir the solution and check the temperature. Care should be taken not to add any further water to the solution or it can become too dilute.

A synthetic urine formulation and methods and kits for making the same are described herein. Alternate components and amounts thereof suitable for use in the described invention will be apparent to practitioners in the art.

EXAMPLES

Dried Urine Composition Kit

A kit comprising a 3 ounce container with screw top, a sealed vial of dried urine composition and a sealed vial of heat activator are provided. The container has a temperature sensitive color gradient and a fill line demarcation (3 ounce) provided thereon. The container is filled with tap water at about room temperature to the fill line, which can be the top of a temperature strip adhered to the container. The dried synthetic urine is carefully added. The container is sealed with the screw top and gently shaken until a urine solution, preferably without sediment results. Heat activator is added slowly with mixing (gentle shaking or swirling) until a desired temperature of about 98° F. is achieved according to the temperature sensor. Any excess heat activator is discarded.

Concentrated Urine Composition Kit

A kit comprising a 3 ounce resealable container with concentrated urine composition and a sealed vial of heat activator are provided. The container has a temperature sensitive color gradient and a fill line demarcation (3 ounce) provided thereon. The container is filled with warm tap water (about 80° F.) to the fill line, which can be the top of a temperature strip adhered to the container. The container is sealed and gently shaken to mix the water and concentrated urine composition, forming a urine solution. Heat activator is added slowly with mixing (gentle shaking or swirling) to the urine solution until a desired temperature of about 98° F. is achieved according to the temperature sensor. Excess heat activator is discarded.

Urine Solution Kit

A kit comprising a 3 ounce resealable container of synthetic urine solution and a sealed pouch of heat activator are provided. The container has a temperature sensitive color gradient provided thereon. Heat activator is added slowly with mixing (gentle shaking or swirling) to the urine solution until a desired temperature of about 98° F. is achieved according to the temperature sensor. Any excess heat activator is discarded.

The above examples are descriptive of certain embodiments of the invention. Other embodiments as described elsewhere herein, and alternative materials and methods as known to practitioners in the art are considered to be within the scope of the invention as claimed below.

I claim:
1. A synthetic urine comprising:
a) a synthetic urine formulation; and
a heat activator
wherein the synthetic urine is within the normal limits of three or more of the indicia characteristic of urine selected from the group consisting of pH, urea concentration, uric acid concentration, creatinine concentration, calcium ion concentration, sodium ion concentration phosphorus ion concentration, potassium ion concentration, and chloride ion concentration and wherein the synthetic urine is within the normal limits of temperature associated with a freshly obtained urine sample.
2. The synthetic urine of claim 1, wherein the synthetic urine formulation is in a dehydrated form.
3. The synthetic urine of claim 1, wherein the synthetic urine formulation is in a concentrated form.

4. The synthetic urine of claim 1, wherein the synthetic urine formulation is a urine solution.

5. The synthetic urine of claim 1, wherein the heat activator is lithium chloride.

6. A method of fanning synthetic urine comprising combining a synthetic urine formulation and a sufficient amount of heat activator to from a synthetic urine with normal human urine characteristics having a temperature of from about 90° F. to about 105° F.

7. The method of claim 6, wherein the synthetic urine formulation is in dehydrated form.

8. The method of claim 6, wherein the synthetic urine formulation is in concentrated form.

9. The method of claim 6, wherein the heat activator is lithium chloride.

10. A kit for forming synthetic urine, the kit comprising:
a mixing container;
a synthetic urine formulation; and
a heat activator,
wherein the synthetic urine is within the normal limits of three or more of the indicia characteristic of urine selected from the group consisting of pH, urea concentration, uric acid concentration, creatinine concentration, calcium ion concentration, sodium ion concentration, phosphorus ion concentration, potassium ion concentration, and chloride ion concentration,
and wherein the synthetic urine is within the normal limits of temperature associated with a freshly obtained urine sample.

11. The kit of claim 10, wherein the synthetic urine formulation is in dehydrated form.

12. The kit of claim 10, wherein the synthetic urine formulation is in concentrated form.

13. The kit of claim 10, wherein the mixing container has a fill line.

14. The kit of claim 10, wherein the mixing container has a temperature indicator.

15. The kit of claim 10, further including a temperature sensing device.

16. The kit of claim 10, wherein the heat activator is lithium chloride.

17. The kit of claim 10, wherein the synthetic urine formulation is in dehydrated form, the heat activator is lithium chloride, the mixing container includes a fill line, and the mixing container includes a temperature indicator.

* * * * *